United States Patent [19]

Goldman

[11] Patent Number: 5,480,889
[45] Date of Patent: Jan. 2, 1996

[54] COMPOSITIONS AND METHODS FOR PROMOTING HAIR GROWTH

[76] Inventor: Boris E. Goldman, 2019 Breton, SE., Grand Rapids, Mich. 49546

[21] Appl. No.: 390,628

[22] Filed: Feb. 17, 1995

Related U.S. Application Data

[63] Continuation of Ser. No. 20,202, Feb. 19, 1993, Pat. No. 5,407,944.

[51] Int. Cl.$^6$ ..................................................... A61K 31/00
[52] U.S. Cl. ........................... 514/310; 514/256; 514/880
[58] Field of Search .................................... 514/310, 256, 514/880; 424/70

[56] References Cited

U.S. PATENT DOCUMENTS

| 4,596,812 | 6/1986 | Chiosey et al. | 54/256 |
| 5,015,470 | 5/1991 | Gibson | 424/70 |

OTHER PUBLICATIONS

Young, M. W., "American Association of Anatomists," *Anatomical Record* 100:728 (1948).
Young, M. W., "American Association of Anatomists," *Anatomical Record* 97:378 (1947).
Szasz, T. S. et al. "A Theory of the Pathogenesis of Ordinary Human Baldness" *Archives of Dermatology and Syphilology* 61:34–48 (1950).
Orentreich, N. "Autografts in Alopecias and Other Selected Dermatological Conditions," *Ann. NY Acad. Sci.* 83:463–479 (1959).
Orentreich, N. et al. "Biology of Scalp Hair Growth," *Clin. Plast. Surg.* 9:197∝205 (1982).
Zapocosta, A. R. "Reversal of Baldness in Patient Receiving Minoxidil for Hypertension," *New Eng. J. Med.* 303:1480–1481 (1980).
Hamilton, J. B. "Patterned Loss of Hair in Man: Types and Incidence," *Ann. NY Acad. Sci.* 53:709–728 (1951).
Klemp, P. et al., "Subcutaneous Blood Flow in Early Male Pattern Baldness," *J. Invest. Derm.* 92(5):725–726 (1989).
Juri, J. et al., "Temporo–Parieto–Occipital Flap for the Treatment of Baldness," *Clin. Plas. Surg.* 9:255–261 (1982).
Lemke, R. et al., "Noninvasive Ptco$_2$ Initial Slope Index and Invasive Ptco$_2$ Arterial Index as Diagnostic Criterion of the State of Peripheral Circulation," *Crit. Care Med.* 16:353–357 (1988).
Kram, H. B. et al., "Assessment of Peripheral Vascular Disease by Postocclusive Transcutaneous Oxygen Recovery Time," *J. Vasc. Surg.* 1:628–634 (1984).
Wester, R. C. et al., "Minoxidil Stimulates Cutaneous Blood Flow in Human Balding Scalps: Pharmacodynamics Mesured by Laser Doppler Velocimetry and Photopulse Plethysmography," *J. Invest. Derm.* 82:515–517 (1984).
Dingman, R. O. et al., "The Surgical Repair of Traumatic Defects of the Scalp," *Clin. Plast. Surg.* 9:131–144 (1982).
Hunt, et al., "The Effect of Varying Ambient Oxygen Tensions on Wound Metabolism and Collagen Synthesis," *Surg. Gyn. Ob.* 135:561–566 (1972).

Marshall, R. C. et al., "Structure and Biochemistry of Mammalian Hard Keratin," 4:47–83 (1991).
Jonsson, K. et al., "Tissue Oxygenation, Anemia, and Perfusion in Relation to Wound Healing in Surgical Patients," *Ann. Surg.* 214:605–613 (1991).
Buxman, M. et al., "Keratin Cross–Linking and Epidermal Transglutaminase," *J. Invest. Dem.* 65:107–112 (1975).
Buxman, M. M. "Enzymes of Keratinization," *Internat. J. Derm.* 20:95–98 (1981).
Sawaya, M. E. et al., "Immunohistochemical Distribution of Aromatase and 3B–hydroxysteroid Dehydrogenase in Human Hair Follicle and Sebaceous Gland," *J. Cutan. Pathol.* 19:309–314 (1992).
Sawaya, M. E. "Steroid Chemistry and Hormone Controls During the Hair Follicle Cycle," *Ann. NY Acad. Sci.* 642:376–383 (1991)(Abstract).
Sawaya, M. E. "Steroid Chemistry and Hormone Controls During the Hair Follicle Cycle," *Ann. NY Acad. Sci.* 642:376–383 (1991).
Schweikert, H. U. et al., "Regulation of Human Hair Growth by Steroid Hormones. 1. Testosterone Metabolism in Isolated Hairs," *J. Clin. Endocrin. Metab.* 38:811–819 (1974).
Orfanos, C. E. "Lokaltherapie der Alopecia Androgentica mit 17 α–Ostradiol," *Dermatologica* 161:124–132 (1980).
Takayasu, S. et al., "The Conversion of Testosterone to 17β–hydroxy–5α–androstan–3–one–(Dihydrotestosterone) by Human Hair Follicles," *J. Clin. Endocrinol. Metab.* 34:1098 1101 (1972).
Anderson, R. D. "Expansion–Assisted Treatment of Male Pattern Baldness," *Clin. Plast. Surg.* 14:477–489 (1987).
Herring, B. D., "Unravelling the Pathophysiology of Male Pattern Baldness," *J. Nation. Med. Assoc.* 77:142 and 145 (1985).
Freedberg, I. M., "Biochemistry of Keratinization in Hair: Protein Synthesis, Pathways and Controls," pp. 105–112 (1989).
Hamilton, J. B., *Am. J. Anat.* 71:451–480 (1942).
Jonsson, K. et al., *Ann. Surg.* 241, 5:605–613 (1991).
Bruchovsky, N. et al., *J. Biol. Chem.* 243:2012 (1968).
Tang, S. et al., *J. Biol. Chem.* 244:6584 (1969).
Thigpen, A. E. et al., *J. Clin. Invest.* 92(2):903–10 (1993).
Mellin, T. N. et al., *J. Steriod Biochem Mol. Biol.* 44(2):121–31 (1993).
Imperato–McGinley, J. et al., *J. Clin. Endocrinol. Metab.* 76(2):524–8 (1993).
Diani, A. R. et al., *J. Clin. Endocrinol. Metab.* 74(2):345–50 (1992).

*Primary Examiner*—Arthur C. Prescott
*Attorney, Agent, or Firm*—Harness, Dickey & Pierce

[57] ABSTRACT

The present invention provides compositions and methods for promoting hair growth. The methods generally comprise the administration to a patient of a therapeutically effective amount of the compositions of the present invention which employ a vasodilator in combination with estradiol and/or a 5-α-reductase inhibitor in a pharmaceutically acceptable vehicle. The compositions and methods of the present invention are suitable for the treatment of baldness, in particular, male pattern baldness.

3 Claims, 2 Drawing Sheets

COMPOSITIONS AND METHODS FOR PROMOTING HAIR GROWTH

This is a continuation patent application Ser. No. 08/020,202 filed Feb. 19, 1993, 5,407,944.

FIELD OF THE INVENTION

The present invention relates generally to compositions and methods for promoting hair growth and, more particularly, to compositions and methods for treatment for baldness. The compositions and methods of the present invention employ two or more agents selected from the group consisting of vasodilators, estradiols and/or 5-α-reductase inhibitors.

BACKGROUND OF THE INVENTION

Male pattern baldness (MPB) affects 60–80% of the male caucasian population with advancing age. Anderson, R. D., *Clin. Plast. Surg.* 1987:14,(3):447. Various etiologies for MPB have been proposed which include age, genetic androgens and scalp tension. In particular, in 1942 and 1951, it was reported that the etiology of MPB was related to an interdependent relationship of age, genetic predisposition and androgens. Hamilton, J. B., *Am. J. Anat.* 1942:71:451–480 and Hamilton, J. B. *Ann NY Acad. Sci.* 1951:53:708. It was found that MPB would not occur unless androgens were present and that androgens would not induce MPB without genetic predisposition. In 1959 it was postulated that MPB was linked to an androgen-sensitive, genetically pre-disposed senescence of hair follicles. These genetically predisposed hair follicles were located in the frontal and crown regions of the scalp. This theory (sometimes called "Donor Dominance") has prevailed for over thirty years.

Most treatment modalities currently employed (such as hair transplantation) have been performed based on this theory. However, transplantation methods are somewhat complex and no single treatment modality has proven completely or repeatably successful in inducing, maintaining and/or increasing hair growth.

More recently, in 1980, the reversal of MPB in a male patient receiving minoxidil for hypertension was revealed and minoxidil has since been used to promote hair growth, most commonly by topical application. Zapacosta, A. R., *N. Eng. J. Med.* 1980:303:1480–1481. Minoxidil's vasodilating effect on the scalp is one of the proposed mechanisms by which minoxidil promotes hair growth. However, despite its popularity, minoxidil has not performed in a completely satisfactory fashion in promoting hair growth in all target populations.

In summary, although various etiologies for baldness have been proposed and many treatments based on these etiologies attempted, the underlying pathophysiologies which cause baldness have not been elucidated. It is clear that without the identification of such pathophysiologies, no single treatment could be developed.

It would thus be desirable to develop a predictable method for treating baldness including male pattern baldness by promoting hair growth. It would also be desirable to develop a method for promoting hair growth based on the here-to-fore unrecognized pathophysiology which appears to cause baldness once identified.

SUMMARY OF THE INVENTION

The present invention provides compositions and methods for promoting hair growth.

The methods of the present invention generally comprise the treatment of a patient (in need of such treatment) with a therapeutically-effective amount of a vasodilator in combination with either an estradiol; or a 5-α-reductase inhibitor or a mixture of all three, preferably for a time sufficient to promote sufficient hair growth. The methods preferably include administration of the selected agents from a pharmaceutically-acceptable vehicle; however, the agents can be concomitantly administered via different modes, e.g., a combination of topical, oral, etc. The methods of the present invention are suitable for the treatment of baldness and, in particular, male pattern baldness.

The compositions of the present invention comprise mixtures of these agents, (a vasodilator plus an estradiol or a 5-α-reductase inhibitor; or a mixture of all three) preferably in a topical or oral unit dosage form.

A better understanding of the present invention and its advantages will be had from a reading of the Detailed Description of the Preferred Embodiments taken in combination with the Drawings and Claims.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

Figure 1:
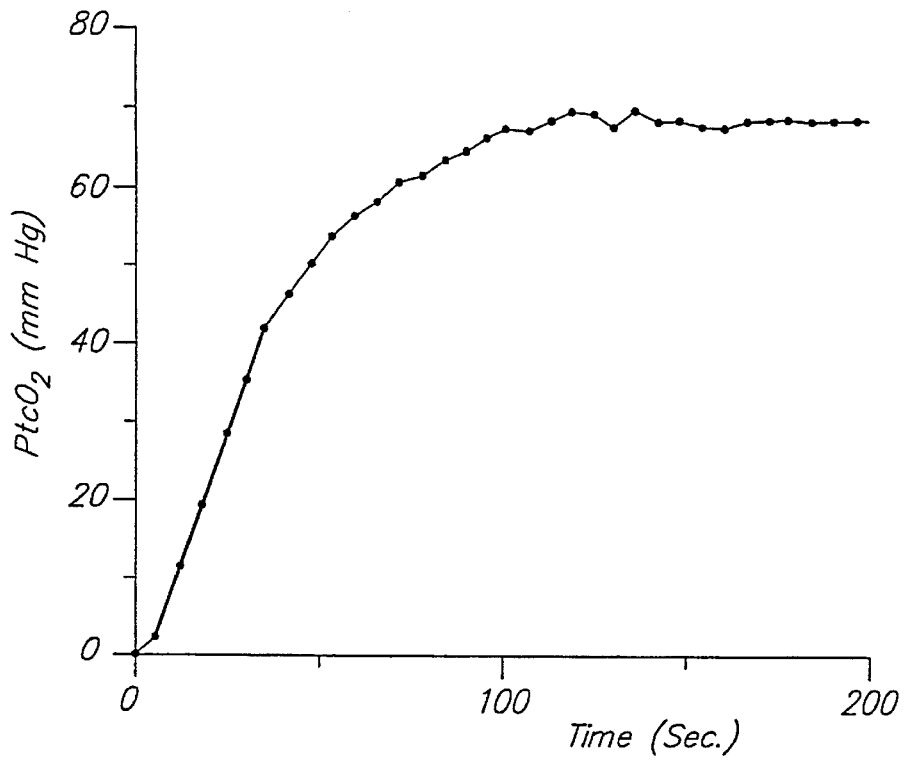
FIG. 1 is a sample plot illustrating the $PtcO_2$ (mm Hg) versus time of a control subject following release of a scalp tourniquet.

The present invention relates to compositions and methods for promoting hair growth. In accordance with the present invention, a therapeutically effective amount of a mixture of agents, preferably comprising a vasodilator in combination with an estradiol and/or a 5-α-reductase inhibitor, is formulated and administered to a patient to promote hair growth. The method of the present invention finds use in any patient (human or other mammal) seeking to induce, maintain or increase hair growth. The method of the present invention is suitable for the treatment of various types of baldness, in particular, male pattern baldness (MPB) or alopecia.

While not intending to be based by theory, it is believed that local tissue hypoxia may be the underlying pathophysiology by which age, genetics and androgens interact to cause baldness. The method of the present invention is based on the recognition of this underlying baldness-inducing pathophysiology.

It should be appreciated that while this invention preferably contemplates topical or oral administration, nothing herein should be construed to limit the mode of delivery. Both topical and systemic routes of delivery may be appropriate, particularly in combination-therapy regimes.

Further, it should also be appreciated that each agent of the combination need not be administered in the same manner, i.e., one or more may be administered topically while another may be administered systemically. It therefore follows that while the agents selected for the methods of the present invention are preferably administered concomitantly, the administration need not be coinstantaneously. It is preferred that they be administered to such that their therapeutical effects are synchronized or overlap. Based upon ease of treatment, however, in a highly preferred embodiment the selected agents are administered from a single vehicle in unit dosage form, including tablet, capsule, and transdermal patches or preparation.

It will be appreciated that the actives useful in the compositions and methods of the present invention may also be employed in pharmaceutically-acceptable forms such as esters, salts, or as pro-drugs.

In practicing the method of the present invention, the amount of vasodilator, estradiol and 5-α-reductase inhibitor to be administered (as well as other factors in the treatment regime) will vary with the patient being treated and will be monitored on a patient-by-patient basis by the physician or other health-care provider. Generally, a therapeutically-effective amount of the compounds of the present invention will be applied for a therapeutically effective duration. By "therapeutically-effective amount" and "therapeutically-effective duration" is preferably meant an amount or duration effective to achieve a selected desired result In accordance with the present invention without undue adverse physiological effects or side effects; the desired result generally being a clinically observable increase in hair growth at the target situs.

Without limitation, it is contemplated that the vasodilators useful in the present invention may operate by any mechanism of action and may preferably be selected from the group consisting of minoxidil, nitroglycerin, diazoxide, or mixtures thereof. Calcium ion influx inhibitors (calcium channel blockers) such as nifedipine, are also contemplated as preferred vasodilators in the present invention.

Minoxidil is chemically described as 2,4-pyrimidinediamine,6-(1-piperidinyl)-,3-oxide and has a molecular weight of 209.25. It is contemplated that minoxidil will be effective when delivered in a topical composition comprising from about 0.01% to about 5% minoxidil and by oral administration in the range of from about 5 to about 100 mg dose per day. A highly preferred topical vasodilator composition is a minoxidil-containing preparation marketed by The Upjohn Company under the registered trademark Rogaine. Rogaine topical solution is available at a concentration of 2% in a solution of (60% v/v) propylene glycol, and water. The preferred dosage of Rogaine solution is about 2 mL per day.

Minoxidil in tablet form (likewise marketed by Upjohn) under the tradename Loniten, is another highly preferred vasodilator. Loniten tablets typically contain from about 2.5 mg to about 10 mg of minoxidil as well as the following inactive ingredients: cellulose, corn starch, lactose, magnesium stearate and silicon dioxide. The preferred dosage of minoxidil is from about 1 to about 300 mg per day. The more preferred dosage is from about 5 to about 100 mg per day. The most preferred dosage is from about 10 to about 40 mg per day.

Another highly preferred vasodilator for use in the compositions and methods of the present invention is nitroglycerin, available from various companies in various forms, i.e. transdermal systems, ointments, oral tablets, sprays, and other delivery forms. Nitroglycerin is chemically described as 1,2,3-propanetriol trinitrate and has a molecular weight of 227.09. A preferred transdermal system is marketed under the trademark Nitro-Dur by Key Pharmaceuticals, Inc. The composition and use of Nitro-Dur is discussed at pages 1191–1192 of the Physicians Desk Reference, 47th ed. (1993) which Applicants herein incorporate by reference.

Another highly preferred vasodilator for use in the compositions and methods of the present invention is diazoxide, marketed by Baker Norton Pharmaceuticals, Inc. under the trademark Proglycem. Diazoxide is chemically described as 7-chloro-3-methyl- 2H-1,2,4-benzothiadiazine1,1-diazoxide. Proglycem is available for oral administration in capsule or suspension form. The preferred dosage of diazoxide is from about 1 to about 24 mg/kg per day. The more preferred dosage is from about 1 to about 16 mg/kg per day. The most preferred dosage is from about 3 to about 8 mg/kg per day.

Another highly preferred vasodilator is nifedipine, marketed by Pfizer Labs under the trademark Procardia. Nifedipine is an antianginal drug belonging to a class of pharmacological agents known as calcium channel blockers. Nifedipine is chemically described as 3,5-pyridinedicarboxylic acid,1,4-dihydro-2,6-dimethyl-4-(2-nitrophenyl),-dimethyl ester. It has an empirical formula represented by $C_{17}H_{18}N_2O_6$ and a molecular weight of 346.3. Procardia is typically employed in capsule form containing 10 mg to 20 mg nifedipine per capsule. Inert ingredients in the formulations include: glycerin; peppermint oil; polyethylene glycol; soft gelatin capsules (which contain Yellow 6, and may contain Red Ferric Oxide and other inert ingredients), and water. The 10 mg capsules also contain saccharin sodium, The preferred dosage of Procardia (nifedipine) is from about 10 to about 120 mg per day. The more preferred dosage is from about 20 to about 100 mg per day. The most preferred dosage is from about 30 to about 60 mg per day.

Other actives in the class of calcium channel blockers are also contemplated as preferred vasodilators in the present invention.

Procardia XL is the trademark for nifedipine GITS (Gastrointestinal Therapeutic System) and is also available through Pfizer Labs. Procardia XL is a tablet formulated as a once-a-day controlled release tablet for oral administration designed to deliver 30, 60 or 90 mg of nifedipine per tablet. Inert ingredients in the formulations include: cellulose acetate; hydroxypropyl cellulose; hydroxypropyl methylcellulose; magnesium stearate; polyethylene glycol; polyethylene oxide; red ferric oxide; sodium chloride and titanium dioxide. A preferred dosage of Procardia XL (nifedipine GITS) is from about 10 to about 90 mg per day. A more preferred dosage of Procardia XL is from about 20 to about 80 mg per day. A highly preferred dosage of Procardia XL is from about 30 to about 60 mg per day.

A highly preferred estradiol for use in the compositions and methods of the present invention include 17 β-estradiol, marketed by Mead Johnson Laboratories under the trademark Estrace. Estradiol is believed to be the most potent physiologic estrogen and is the major endogenous estrogenic hormone. 17 β-estradiol is chemically described as estra-1, 3,5(10)-triene-3,17 β-diol. Estrace is commercially available in tablet or cream form. The estradiol in Estrace tablets has been micronized and is rapidly and effectively absorbed from the gastrointestinal tract according to Mead. Estrace tablets which contain 1 mg of estradiol also contain the following inactive ingredients: acacia, D&C Red No. 27 (aluminum lake), dibasic calcium phosphate, FD&C Blue No. 1 (aluminum lake), lactose, magnesium stearate, colloidal silicon dioxide, starch (corn) and talc. Estrace tablets which contain 2 mg of estradiol also contain the following inactive ingredients: acacia, dibasic calcium phosphate, FD&C Blue No. 1 (aluminum lake), FD&C Yellow No. 5 (tartrazine) (aluminum lake), lactose, magnesium stearate, colloidal silicon dioxide, starch (corn) and talc. Each gram of Estrace in cream form contains 0.1 mg estradiol in a nonliquefying base containing purified water, propylene glycol, stearyl alcohol, white ceresin wax, glyceryl monostearate, hydroxypropyl methylcellulose, 2208 4000 cps, sodium lauryl sulfate, methylparaben, edetate disodium and tertiary-butylhydroquinone.

The preferred dosage of estradiol in tablet form is from about 1 to about 90 mg micronized estradiol per day. A more preferred dosage is from about 1 to about 60 mg micronized estradiol per day. A highly preferred dosage is from about 1 to about 30 mg micronized estradiol per day. A preferred dosage of Estrace in cream form is from about 1 to about 12 g (about 0.1 to about 1.2 mg estradiol) per day. A more preferred dosage is from about 1.5 to about 8 g (about 0.15 to about 0.8 mg estradiol) per day. A highly preferred dosage is from about 2 to about 4 g (about 0.2 to about 0.4 mg estradiol) per day.

Another highly preferred estradiol is an estradiol transdermal system marketed by CIBA Pharmaceutical Company under the registered trademark Estraderm. Estraderm is designed to release 17 β-estradiol through a rate limiting membrane continuously upon application to intact skin. Estraderm is available in two dosage systems, to provide nominal in vivo delivery of 0.05 or 0.1 mg of estradiol per day via skin of average permeability. The system providing 0.05 mg of estradiol per day has a contact surface of 10 cm$^2$, contains 4 mg of estradiol USP and 0.3 ml of alcohol USP. The system providing 0.1 mg of estradiol per day has a contact surface area of 20 cm$^2$, contains 4 mg of estradiol USP and 0.6 ml of alcohol USP.

A highly preferred inhibitor of the steroid 5-α-reductase for use in the compositions and methods of the present invention, is a synthetic 4-azasteroid compound marketed by Merck & Co., Inc. under the registered trademark Proscar; this active is also called finasteride. Finasteride is 4-azaandrost-1-ene-17-carboxamide, N-(1,1-dimethylethyl)-3-oxo-, (5α, 17β)-. It has an empirical formula represented by $C_{23}H_{36}N_2O_2$ and a molecular weight of 372.55. Proscar tablets contain 5 mg of finasteride as well as the following inactives: docusate sodium, FD&C Blue 2(aluminum lake), hydrous lactose, hydroxypropyl cellulose LF, hydroxypropylmethyl cellulose, magnesium stearate, microcrystalline cellulose, pregelatinized starch, purified water, sodium starch glycolate, talc, titanium dioxide and yellow iron oxide. The preferred dosage of Proscar (finasteride) is from about 0.5 to about 15 mg per day. The more preferred dosage is from about 3 to about 10 mg per day. The most preferred dosage is from about 4 to about 6 mg per day.

It should be appreciated that duration of treatment according to the methods of the present invention will vary with many factors and will primarily depend upon the specific condition of the patient, the target situs, and the specific combination of agents employed. It should also be appreciated that both treatment agents, dosage and duration will be interdependent and can be varied together in order to achieve an optimal clinical response. In addition, dosage and duration will also depend on the specific combination of agents employed.

The agents utilized in the compositions and methods of the present invention can be administered in accordance with the present invention in any pharmaceutically-acceptable carrier, preferably one which is both non-toxic and suitable for topical or systemic delivery. The compounds may be formulated for administration by procedures well-established in the pharmaceutical arts.

For topical administration, pharmaceutically-acceptable vehicles in the form of creams, oils, ointments, gels, pastes, liquids, powders, sprays, dips, transdermal patches, and other delivery modes known to those skilled in the art may be utilized. A topical vehicle or vehicle component is generally "pharmaceutically-acceptable" if the vehicle or component does not substantially interfere with the pharmacological activity of the agent or agents and does not cause undue side effects.

The agents may also be employed in unit dosage forms. These can comprise about 1 to about 500 mg of vasodilator; about 1 to about 150 mg of estradiol, and/or about 0.1 to about 50 mg of 5-α-reductase inhibitor.

For example, a pharmaceutical preparation in unit dosage form adapted for administration to promote hair growth may be prepared comprising, per unit dosage, at least two active agents selected from the group consisting of minoxidil, estradiol and finasteride each in an effective non-toxic amount within the range of from about 1 to about 300 mg minoxidil; about 1 to about 90 mg estradiol; and about 0.5 to about 15 mg finasteride.

Such unit dosage preparations may be adapted for oral administration as a tablet, capsule, liquid, powder, bolus or the like. They may likewise be prepared in unit dosage form in an ingestible or injectable or topical form.

Art-disclosed formulation ingredients such as tableting agents, colorants, flavorants, anti-oxidants, emollients, surface-active agents, encapsulation agents, and the like may also be employed.

All percentages (%) herein are percentages by weight unless otherwise indicated or apparent from the context of use. The term "comprising" as used herein includes the more limiting terms of "consisting essentially of" and "consisting of."

The following Examples and Discussion of Results further describe the compositions and methods of the present invention.

EXAMPLE 1

A study was performed to determine if there is a relative microvascular insufficiency and associated tissue hypoxia to regions of bald scalp in men with male pattern baldness as compared to hair bearing scalp in men with no baldness.

Eighteen male volunteers (age ≧18 years old), all of which were non-smokers, were used in the study. Nine of the men had MPB, with either Juri degree II or III (fronto-parietal or fronto-parietal-crown baldness). Juri, J. et al., *Clin. Plast. Surg.* 1982:9:255. Nine of the men were controls, with no MPB. Both groups had similar mean ages, the mean age of the bald subjects was 33.8 years ±2.3; while the mean age of the control subjects was 28.6 years ±0.6. All measurements were obtained while the subjects were seated with an ambient temperature of about 25–30 degrees centigrade.

Frontal and temporal measurement sites were used in each subject. To consistently place the frontal site, a nasion to occipital protuberance distance was obtained in all subjects. The frontal site was then placed at 31% of the nasion to occipital protuberance distance in the midline, as measured from the nasion. This distance placed the measurement site well behind the hair line in all of the controls. The temporal site was placed in the left temporal hair bearing region immediately superior to the helix of the left ear. A First Temp Thermometer (Intelligent Medical Systems Inc., Carlsbad, Calif.) was used to measure the surface temperature at each site in each subject. A 1.5 cm diameter circle was shaved at each site in all subjects (villus hair was shaved in the frontal region of the bald subjects). Sites were cleansed with an alcohol pad, and a transcutaneous $PO_2$ sensor (SensorMedics Corp., Yorba, Calif.) was placed at each site. Sensors were affixed to the skin with double-sided adhesive rings and a small drop of sterile $H_2O$ as the contact medium. The sensor characteristics included a 90% response time ($T_{90}$) of 12 seconds, and an accuracy of ±3 mm Hg a 90 mm $HgO_2$. Each transcutaneous $PO_2$ monitor was calibrated on the same base station prior to use on each subject. The sensors were set at an operating temperature of 43 degrees centigrade.

Resting $PtcO_2$ was obtained at each site. A scalp tourniquet was then applied until the $PtcO_2$ decreased to<2 mm Hg (±2 mm Hg). Temporal scalp pressure was applied as needed to produce ischemia of the entire scalp. The tourniquet was released and $PtcO_2$ readings were obtained every 6 seconds providing a sufficient number of data points within the $T_{90}$ of the transcutaneous $PO_2$ monitor. Data was analyzed by Repeated Measures Analysis of Variance, with significance assessed at $p<.05$. A BLSD test was then performed to determine differences between individual means, with significance assessed at $p<.05$. (Data is presented as mean ±standard error in mean (SEM)).

The advantage of using the transcutaneous $PO_2$ ($PtcO_2$) method for evaluating the circulation of the scalp is that it is non-invasive and provides a direct measure of the tissue (dermal) $PO_2$ surrounding the hair follicles. In addition, by placing a probe in the frontal and temporal regions of the scalp, bald and hair bearing scalp in the same MPB subject was compared to control subjects. Also, studies have shown that the transcutaneous $PO_2$ can be used to assess the state of peripheral circulation. This is based on the principle that a region with insufficient peripheral blood flow will have a prolonged post-occlusive $PtcO_2$ recovery time. Lemke, R. et al., *Critical Care Medicine* 1988:16(4):353–357 and Kram, H. B. et al., *J. Vasc. Surg.* 1984:1 (5):628–834. In turn, post occlusive maximum initial slope ($dPtcO_2/dt$) should be proportional to the blood flow of a given region of scalp.

$PtcO_2$ versus time was plotted for each site, a tangent to the steepest portion of the curve was drawn, and a maximum initial slope calculated. FIG. 1 depicts a sample plot of $PtcO_2$ (mm Hg) versus time (sec) from the temporal region of a control subject following release of the scalp tourniquet. The shaded line in FIG. 1 represents the steepest initial portion of the curve used for slope calculations. All graphing and slope calculations were performed by computer, using a Cricket graph 2.0 program on a Macintosh IIci.

Figure 2:
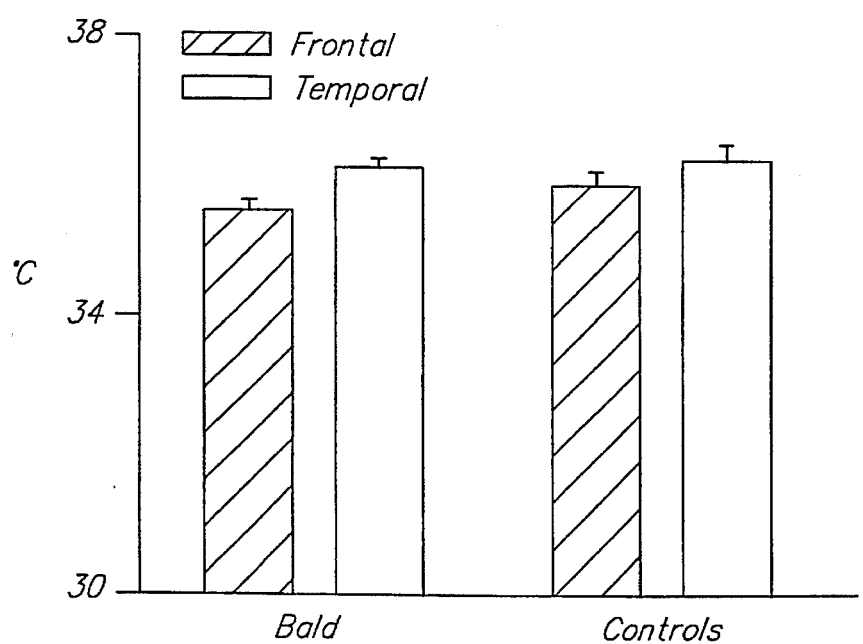
FIG. 2 is a bar graph illustrating the frontal and temporal scalp temperature of bald and control subjects.

Scalp temperatures were also recorded in order to determine if there was a difference in temperature between bald scalp and hair bearing scalp in the bald subjects compared to controls. As shown in FIG. 2, the temporal scalp temperature was statistically significantly higher (approximately 1° F. (0.6°–1.1° F.)) than frontal scalp temperature in both bald subjects and controls. However, there was no significant difference in scalp temperatures between bald subjects and controls. Thus, any differences in scalp blood flow and $PtcO_2$ observed between bald subjects and controls can not be attributed to differences in scalp temperature.

Figure 3:
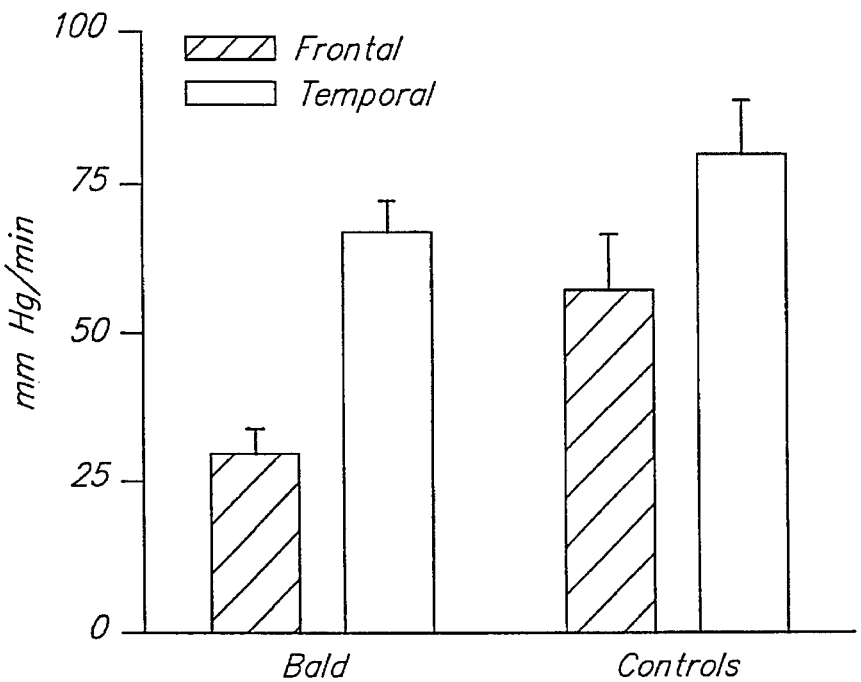
FIG. 3 is a bar graph illustrating the maximum initial slopes ($dPtcO_2/dt$ [mm Hg/min]) of the frontal and temporal scalps of bald and control subjects.

FIG. 3 illustrates the maximum initial slopes ($dPtcO_2/dt$ [mm Hg/min]) of the frontal and temporal scalps of the nine bald and nine control subjects. Slopes were calculated from the initial steepest portion of the post occlusive $PtcO_2$ versus time for each scalp region in each subject. Scalp blood flow, which is proportional to maximum initial slope (d $PtcO_2/dt$), was significantly lower in the bald subjects relative to controls. Comparing individual slopes reveals that in the bald subjects the frontal (non-hair bearing region) blood flow (30.3±3.93) was significantly less than the temporal (hair bearing region) blood flow (66.8±5.40). In control patients, there was no significant difference between the frontal blood flow (56.3±9.32) and the temporal blood flow (79.2±8.94). Although comparing the frontal blood flow in the bald and control patients did not yield a significant difference ($p>.05$), the bald frontal slope was 54% lower than that of the controls.

Figure 4:
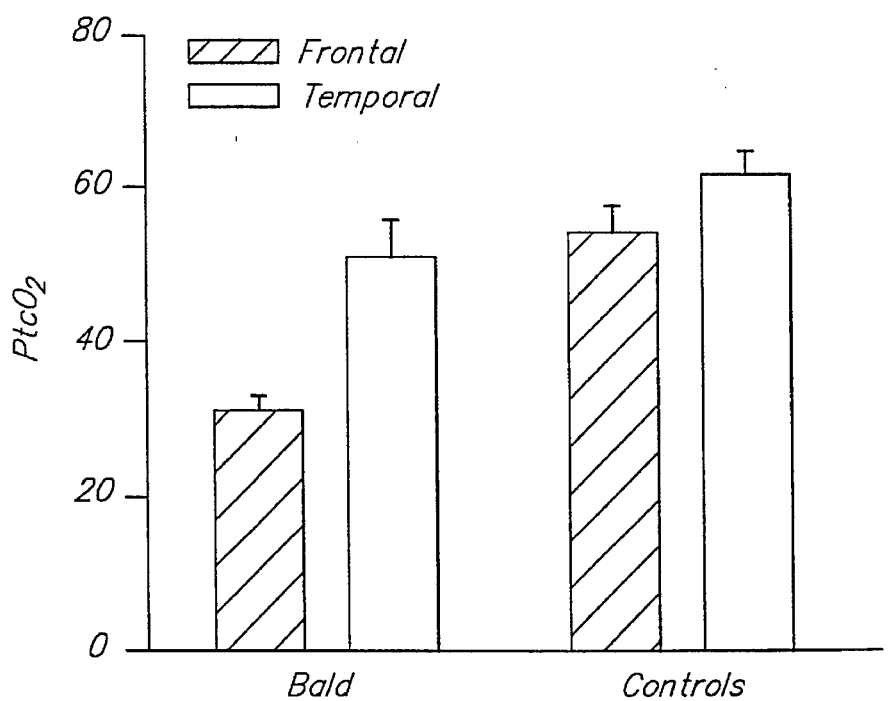
FIG. 4 is a bar graph illustrating the resting transcutaneous $PO_2$ of the frontal and temporal scalps of bald and control subjects.

FIG. 4 represents the resting transcutaneous $PO_2$ ($PtcO_2$ mm Hg) of the frontal and temporal scalps of the nine bald subjects and nine controls. As shown, resting transcutaneous $PO_2$ ($PtcO_2$) was significantly lower in bald frontal scalp (32.2 mm Hg±2.0) than hair bearing temporal scalp (51.8 mm Hg±4.4) in men with MPB. In controls, there was no statistically significant difference in $PtcO_2$ of frontal scalp (53.9 mm Hg±3.5) and temporal scalp (61.4 mm Hg±2.7). Further, in bald subjects the frontal scalp $PtcO_2$ was also significantly lower (32.2 mm Hg±2.0) than in either frontal or temporal scalp of the controls (53.9 mm Hg±3.5 & 61.4 mm Hg±2.7, respectively). Finally, the $PtcO_2$ of the temporal scalps was not significantly different between bald and control subjects (51.8 mm Hg±4.4 & 61.4 mm Hg±2.7, respectively).

Overall, scalp blood flow of control subjects was significantly greater than that of MPB subjects. Klemp et al., using a Xenon washout technique, also found that subcutaneous blood flow to normal scalps was greater than that of MPB patients. In addition, the present study was also able to document that the temporal blood flow is significantly greater than the frontal blood flow in MPB subjects; while in control subjects there was no significant difference between frontal and temporal regions. Also, there was no significant difference between blood flow to the temporal regions in MPB subjects and controls. Finally, a previously unknown local tissue hypoxia in bald scalp compared to hair bearing scalp was identified.

EXAMPLE 2

In order to study the effectiveness of the compounds of the present invention, a prospective double blind study is performed. Men with early male pattern baldness are randomized to one of four groups. The first group of subjects are treated with a topical preparation consisting of a vasodilator only (i.e. minoxidil, nitroglycerin, diazoxide, nifedipine). The second group are treated with a mixture of a vasodilator plus estradiol. The third group are treated with a mixture of a vasodilator, estradiol, and a 5-α-reductase inhibitor (i.e. finasteride). The fourth group are controls, treated with carrier only (no actives). A fifth group is treated with a mixture of a vasodilator and a 5-α-reductase inhibitor. Hair growth is measured at fixed intervals of time, based on standard protocols. Analysis of variance, with significance assessed at $p<.05$ is used to identify statistically significant differences between the treatment groups.

DISCUSSION OF RESULTS

Due to anatomical considerations, there is a relative microvascular insufficiency to regions of the scalp that lose hair in MPB. The scalp is not avascular in bald subjects; however, there is a relative microvascular insufficiency to those regions that lose hair compared to those that do not, and this results in a relative local tissue hypoxia below the level needed for hair growth. The following suggests that a local tissue hypoxia may be the underlying pathophysiology by which age, genetics, and androgens interact to cause MPB. Thus, improving local tissue $PO_2$ of the frontal and crown scalp may be a prerequisite to preventing or reversing early MPB. This might be accomplished medically or surgically. However, a combined treatment of vasodilator, estradiol and/or a 5-α-reductase inhibitor presently represents the optimum medical treatment for early MPB.

Anatomy. Due to the underlying anatomy, there is a relative microvascular insufficiency to regions of the scalp which lose hair in MPB, which is associated with a local tissue hypoxia in those regions. The vascular supply of the scalp is derived from branches of the internal carotid artery and branches of the external carotid artery. Dingman, R. O. et al., *Clin. Plast. Surg.* 1982:9:131. The frontal region of the scalp, which loses hair in MPB, is primarily supplied by the supraorbital and the supratrochlear arteries. These are relatively small branches of the internal carotid artery system. The temporal and occipital regions of the scalp, which do not lose hair in MPB, are supplied by larger branches of the external carotid artery. Specifically, these are the superficial temporal, posterior auricular, and occipital arteries. Further, the frontal and vertex regions of the scalp overly the galea aponeurotica, which is relatively avascular. The temporal and occipital regions of the scalp overly the temporalis and occipitalis muscles, which provide a rich network of musculocutaneous perforator blood vessels. These anatomical differences contribute to the tenuous nature of the dermal blood supply to the frontal and crown regions of the scalp.

One of the early manifestations of vascular insufficiency of the lower extremities is hair loss. The mechanism by which vascular insufficiency causes hair loss is not known. However, Hunt and Pai showed that collagen syntheses by fibroblasts is significantly compromised when tissue $PO_2 < 40$ mm Hg. Hunt T. K. et al., *Surg. Gynecol. Obstet.* 1972:135:351. There may be an analogous situation with keratin production by hair follicle cells.

Keratin Synthesis. The normal scalp has roughly 100,000 hairs, with a 2–6 year anagen phase (growth phase) and roughly a 3 month telogen phase (rest phase). Hair fiber formation is a dynamic process which requires cell proliferation, cell movement, and cell migration. Marshall, R. C. et al., *Microsc.* 1991:Rev, Vol. 4(1):47–83. Human hair is made up of hard α-keratin, a protein which is rich in the amino acid cysteine (10–14% cysteine). Lehninger, A. L., *Biochemistry*, 3rd ed; 1988:126–135. Keratin, like collagen, is composed of multistrand structures in which peptide chains arranged in an α-helix are wound around each other in a tertiary super coil structure and stabilized by covalent cross links. Devlin, T. M. *Textbook of Biochemistry with Clinical Correlations.* 3rd ed. 1991:66–67. It has been shown that the mechanical strength, elastic property and biological resistance of keratins stem directly from the three dimensional structure stabilized by the formation of disulfide bonds. The stabilization of keratin involves the oxidation of cysteine sulfhydryl residues to give cysteine disulfide bonds, primarily between protein chains. The formation of these disulfide cross links lead to the production of a mature hair fiber.

Thus, the stabilization of the tertiary structure of keratin and ultimate maturation of the hair fiber depends on the oxidative formation of disulfide bonds. This oxidative reaction likely requires oxygen. As described in Example 1, there is a local tissue hypoxia to regions of the scalp that lose hair in MPB. This local tissue hypoxia may result in decreased mature keratin production and thus manifest as diminished hair fiber formation. Hunt and Pai, supra, have found that in a hypoxic environment collagen synthesis is significantly decreased. Studies have also shown that prolyl-4-hydroxylase, the enzyme which hydroxylates proline and ultimately allows for the cross linking and stabilization of collagen, has a $K_m$ ($O_2$) of approximately 20–25 mm Hg. Jonsson, K. et al., *Ann Surg.* 1991:314(5):605–613. That is, at a tissue $PO_2$ of 20–25 mm Hg, the enzyme is only operating at 50% of maximal velocity. In the subjects of the study described in Example 1, with MPB, the bald frontal scalp had a $PtcO_2$ of 32.2 mm Hg.

It is not yet clear which critical enzyme in keratin disulfide bond formation is affected in an hypoxic environment. However, Buxman has proposed that γ-glutamyl transpeptidase may be the enzyme involved in the disulfide crosslinking of keratin. Histochemically, the enzyme is localized to the keratinizing region of the hair follicle and is only present during anagen phase. Buxman, M. M. *Int. J. Dermatol.* 1981:20(2):95–98. γ-Glutamyl transpeptidase may be the key point at which hypoxia interferes with mature cross-linked α-keratin and hair fiber formation. Given the inherent similarity between collagen and keratin, it is reasonable to presume that the inability to form covalent cross links in a hypoxic environment will result in decreased keratin deposition similar to that found with collagen. Decreased keratin deposition would result in decreased hair growth just as decreased wound healing was seen by Hunt and Pai when collagen deposition was decreased.

Androgens. Androgens are also involved in the development of MPB. The androgenetic theory to date as expressed by Orentreich, implies that the hair follicles in the crown and frontal regions are genetically different than those located in the temporal and occipital regions. In turn, with androgen stimulation, these genetically predisposed hair follicles become senescent.

In males, the majority of testosterone is synthesized in the testis. The rate limiting step in the production of testerone is the conversion of cholesterol to pregnenolone by the $\gamma^5$ pathway. This rate-limiting step requires NADPH and $O_2$, both of which should be abundant in the testis. Testosterone is then peripherally converted to two active metabolites, dihydrotestosterone and estradiol. Studies have documented that dihydrotestosterone (DHT) is the tissue active androgen and the cellular mediator of androgen action. Bruchovsky, N. et al., *J. Biol. Chem.* 1968:243:2012, Fang. S. et al., *J. Biol Chem.* 1969:244:6584 and Wilson J. D. et al., *Williams Textbook of Endocrinology.* 8th ed. 1992:805–809. The DHT-receptor complex is responsible for external virilization and development of most male secondary sex characteristics. The conversion of testosterone to DHT requires the enzyme reductase activity (as well as NADPH). Takayasu, S. et al., *JCE&M* 1972:34(6):1098–1101. Estradiol production from testosterone also occurs in the periphery and recent immunohistochemical studies have revealed that the aromatase enzyme is present in hair follicles, with accentuated staining during anagen phase. Sawaya, M. E et al, *J. Cutaneous. Pathol.* 1992:19(4):309–314. The aromatization of testosterone requires hydroxylation and oxidation.

Testosterone synthesis in MPB subjects should not be affected by scalp hypoxia, since the majority of testosterone in males is produced in the testis. In the hypoxic environment of the bald scalp, DHT synthesis should not be significantly impaired. Schweikert and Wilson have documented that 5-α-reduction of testosterone to DHT was increased in hair roots from the frontal scalps of balding individuals as compared to other hair bearing scalp sites in the same individuals or to frontal hair roots from women and non-balding men. Schweikert, H. U. et al., *JCE&M* 1974:38(5):811–89. Estradiol synthesis, however, should be stoichiometrically decreased in a hypoxic environment. Three moles of oxygen are required to convert one mole of testosterone to one mole of estradiol. In a hypoxic region, the ratio of DHT to estradiol (DHT/estradiol) should be increased. Sawaya has shown that men with MPB have nearly a two fold increase in 5-α-reductase activity of hair follicles in balding frontal scalp, than in hair bearing occipital scalp. However, hair follicles in the frontal region had nearly three times less aromatase activity than hair follicles in the occipital region in men with MPB. Sawaya, M. E. *Ann. N.Y. Acad. Sci.* 1991:642:376–383. Finding that the DHT/estradiol ratio is elevated in bald scalp as compared to hair bearing scalp in MPB subjects, is consistent with what would be expected in a hypoxic tissue environment.

If one were to develop a gradual local tissue hypoxia of the frontal scalp, the DHT/estradiol ratio might increase locally to a critical level at which point receptor hormone interactions might result in down regulation or inhibition of hair follicle cell function. In turn, this might result in the ultimate conversion of terminal hair to villus hair, and the development of MPB. This inhibition may take the form of altering the number of hair follicle cells in anagen phase as compared to telogen phase.

Orfanos and Vogels, in a controlled, randomized, double blind study, found that application of .025% estradiol for 6 months in subjects with MPB results in a decrease in the number of telogen hairs in 63% of those treated. A similar reduction was found in only 37% of the controls. No regrowth of new hair was found in either group. Orfanos. C. E., et al., *Dermatologica* 1980:161(2):124–132. The addition of estradiol to bald scalp would serve to locally decrease the DHT/estradiol ratio, This appears to decrease the number of hair follicles in resting phase. However, the delivery of adequate $O_2$ would be required to achieve keratin synthesis and hair growth. Thus, it is not surprising that hair regrowth did not occur with the addition of estradiol alone to bald scalps, without concomitant measures to correct the local tissue hypoxia.

Hair Follicle Genetics. In contrast to the "Donor Dominance" theory, hair follicles in the frontal and crown regions of the scalp may not be genetically different from those in the temporal and occipital regions. Rather, a local tissue hypoxia may alter the local hormonal milieu, specifically the DHT/estradiol ratio, and thus account for the androgen stimulated difference in hair production in these regions in MPB subjects.

The clinical observation of progressive lower extremity hair loss in patients with peripheral vascular disease of the lower extremities favors a tissue hypoxia theory. A donor dominance theory for hair loss in this clinical scenario, would imply that the hair follicles in the tibial region are genetically predisposed to lose hair while those in the thigh region are not in patients with distal lower extremity vascular disease. In Orentreich's original experiment (1959), bald scalp transplanted to hair-bearing scalp did not grow. This may have occurred because the hair follicles in the bald scalp were irreversibly atrophic from chronic hypoxia. The fact that autografts from hair bearing scalp grew hair when transplanted to bald scalp appears to be contradictory. However, when transplanting hair bearing autografts, an incision is made in the scalp at the recipient site. This adds the confounding variable of neovascularization in that region. This neovascularization may provide sufficient $O_2$ to allow the local hormonal milieu to be permissive for hair growth.

Hamilton has clearly documented that genetics play an important role in MPB. However, its role may be more specifically related to the genetic predisposition for a particular vascular anatomy or the predisposition for small vessel disease, than to differences between individual hair follicles.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the specification and following claims.

What is claimed is:

1. A pharmaceutical preparation in unit dosage form adapted for administration to promote hair growth comprising, per dosage unit, at least two active agents selected from the group consisting of nitroglycerin, estradiol and finasteride in an effective nontoxic amount.

2. The pharmaceutical preparation of claim 1, wherein the unit form is adapted for oral administration.

3. The pharmaceutical preparation of claim 2, wherein the form adapted for oral administration is a tablet.

* * * * *